United States Patent [19]
Prücher et al.

[11] Patent Number: 4,970,217
[45] Date of Patent: Nov. 13, 1990

[54] OXAZOLIDINONES

[75] Inventors: Helmut Prücher, Heppenheim; Henning Böttcher, Darmstadt; Rudolf Gottschlich, Reinheim; Klaus-Otto Minck, Ober-Ramstadt; Anton Haase, Mühltahl; Christoph Seyfried, Jugenheim, all of Fed. Rep. of Germany

[73] Assignee: Merck Patent Gesellschaft mit beschrankter Haftung, Darmstadt, Fed. Rep. of Germany

[21] Appl. No.: 219,634

[22] Filed: Jul. 15, 1988

[30] Foreign Application Priority Data

Jul. 18, 1987 [DE] Fed. Rep. of Germany ....... 3723797

[51] Int. Cl.$^5$ ................... A61K 31/445; C07D 401/06
[52] U.S. Cl. ..................... 514/327; 546/209; 514/326; 514/330; 514/331
[58] Field of Search ................ 546/204; 514/326, 327, 514/330, 331

[56] References Cited

U.S. PATENT DOCUMENTS 3,457,267  7/1969  Lunsford et al. ................... 546/209
3,821,234  6/1974  Koppe et al. ........................ 546/209
3,856,962  12/1974  Alphin et al. ....................... 514/326

FOREIGN PATENT DOCUMENTS 1951273  10/1969  Fed. Rep. of Germany .

OTHER PUBLICATIONS

*Chemical Abstracts* 73:25438u (1970), Abstract of German Patent 1,951,273 (5/6/70).
Duncan et al., "Aroylpiperidines and Pyrrolidines, A New Class of Potent Central Nervous System Depressants", J. Med. Chem., vol. 13, No. 1, pp. 1–6, (Jan. 1970).

*Primary Examiner*—Glennon H. Hollrah
*Assistant Examiner*—Mark W. Russell
*Attorney, Agent, or Firm*—Millen, White & Zelano

[57] ABSTRACT

Novel oxazolidinones of the formula I

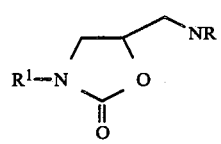

in which R is

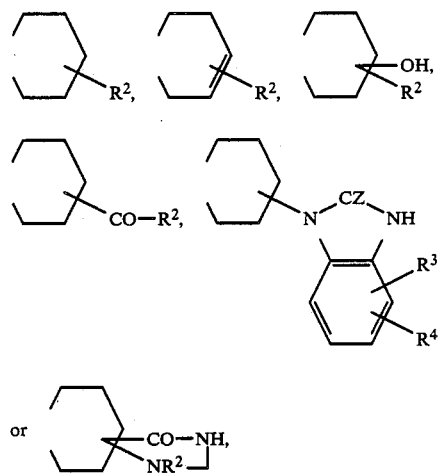

Z is O or S,
$R^1$ and $R^2$ are each phenyl or benzyl radicals which are unsubstituted or mono- or disubstituted by alkyl, alkoxy, alkylthio, alkylsulfinyl and/or alkylsulfonyl having each 1–4 C atoms, alkanoyloxy and/or alkanoylamino having each 1–6 C atoms, F, Cl, Br, OH and/or $CF_3$ or are heteroaryl radicals containing 1–4 heteroatoms and $R^3$ and $R^4$ are each H, alkyl or alkoxy having each 1–4 C atoms or are F, Cl, Br, OH or $CF_3$, and also their salts have effects on the central nervous system, in particular neuroleptic effects.

8 Claims, No Drawings ial

OXAZOLIDINONES

BACKGROUND OF INVENTION

The invention relates to new oxazolidinones of the formula I $$R^1-N\underset{O}{\overset{O}{\underset{\|}{\bigcirc}}}\diagup CH_2NR \quad I$$

in which R is

[cyclohexyl-R², cyclohexenyl-R², cyclohexyl(OH)(R²),
cyclohexyl-CO—R², cyclohexyl-N(CZ-NH-phenyl-R³,R⁴ ring)]

or

[cyclohexyl-CO—NH, NR²⟶]

Z is O or S,

R¹ and R² are each phenyl or benzyl radicals which are unsubstituted or mono- or disubstituted by alkyl, alkoxy, alkylthio, alkylsulfinyl and/or alkylsulfonyl having each 1–4 C atoms, alkanoyloxy and/or alkanoylamino having each 1–6 C atoms, F, Cl, Br, OH and/or CF₃ or are heteroaryl radicals containing 1–4 heteroatoms and R³ and R⁴ are each H, alkyl or alkoxy having each 1–4 C atoms or are F, Cl, Br, OH or CF₃, and also salts thereof.

SUMMARY OF THE INVENTION

An object of the invention was to find novel compounds which can be used for preparing medicaments.

Upon further study of the specification and appended claims, further objects and advantages of this invention will become apparent to those skilled in the art.

These objects have been satisfied by the provision of compounds of the formula $$R^1-N\underset{O}{\overset{O}{\underset{\|}{\bigcirc}}}\diagup CH_2NR$$

wherein R is

-continued

[cyclohexyl-R², cyclohexenyl-R², cyclohexyl(OH)(R²),
cyclohexyl-CO—R², cyclohexyl-N(CZ-NH-phenyl-R³,R⁴ ring)]

or

[cyclohexyl-CO—NH, NR²⟶]

Z is O or S,

R¹ and R² are each independently phenyl or benzyl or phenyl or benzyl mono- or disubstituted by $C_{1-4}$-alkyl, $C_{1-4}$-alkoxy, $C_{1-4}$-alkylthio, $C_{1-4}$-alkylsulfinyl, $C_{1-4}$-alkylsulfonyl, $C_{1-6}$-alkanoyloxy, $C_{1-6}$-alkanoylamino, F, Cl, Br, OH, CF₃ or a mixture thereof, or are heteroaryl with 1–9 carbon atoms, containing 1–4 heteroatoms, and R³ and R⁴ are each independently H, $C_{1-4}$-alkyl, $C_{1-4}$-alkoxy, F, Cl, Br, OH or CF₃, or a physiologically acceptable salt of said oxazolidinones.

DETAILED DISCUSSION

It has been found that the substances mentioned have valuable pharmacological properties in combination with a high tolerance. Thus, they have, for example, a preferably calming (for example sedating, tranquilizing, neuroleptic and/or antidepressant) effect on the central nervous system. Specifically, the compounds have a calming effect on the behavior of mice (for methodics compare Irwin, Psychopharmacologia 13 (1968), 222–257), inhibit the apomorphin-induced climbing behavior in mice (for methodology compare Costall and others, European J. Pharmacol. 50 (1968), 39–50) or induce contra-lateral rotation behavior in Hemiparkinson rats (detectable by the method of Ungerstedt and others, Brain Res. 24 (1970), 485–493) without the occurrence of any significant cataleptic side effects (for methodics compare Dolini-Stola, Pharmakopsychiat. 6(1973), 189–197). Furthermore, the substances inhibit the binding of tritium-labelled dopamine agonists and dopamine antagonists to striatal receptors (detectable by the method of Schwarcz and others, J. Neurochemistry 34 (1980), 772–778, and Creese and others, European J. Pharmacol. 46 (1977), 377–381). In addition, the compounds inhibit the tongue-jaw reflex in the anesthetized rat (detectable by following the methods of Barnett and others, European J. Pharmacol. 21 (1973), 178–182 and of Ilhan and others, European J. Pharmacol. 33 (1975), 61–64). Furthermore, analgesic and hypotensive actions are observed; thus, in catheterized alert, spontaneously hypertonic rats (strain SHR/NIH-MO//CHB-EMD; for the method compare Weeks and Jones, Proc. Soc. Exptl. Biol. Med. 104 (1960), 646–648), the arterial blood pressure measured directly is lowered after the intragastric application of the compounds.

Compounds of the formula I and their physiologically safe acid addition salts can therefore be used as active substances for medicaments and also as intermediates for preparing other active substances of medicaments.

The invention relates to oxazolidinones of the formula I and their salts.

The invention further relates to a process for preparing oxazolidinones of the formula I and also of salts thereof, characterized in that a compound of the formula II

    II in which
Ox is the radical

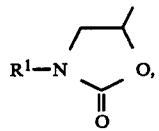

$X^1$ is X or $NH_2$,
X is Hal, OH or a reactive functionally modified OH group and
Hal is Cl, Br or I and
$R^1$ has the meaning given,
is reacted with a compound of the formula III

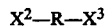    III in which
$X^2$ and $X^3$ are identical or different and, if $X^1$ is $NH_2$, are each X, otherwise together they are NH and
R has the meaning given, and/or that a compound which otherwise corresponds to the formula I but contains, instead of one or more hydrogen atoms, one or more reducible groups and/or one or more additional C—C and/or C—N bonds is treated with a reducing agent and/or that in order to prepare a compound of the formula I in which R is

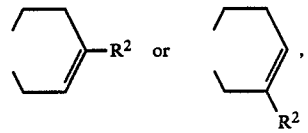

a compound of the formula IV

    IV in which
$R^5$ is

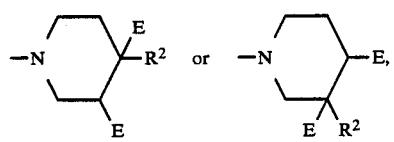

one radical E is X, CN or $NH_2$, the other radical E is H and

Ox, $R^2$ and X have the meanings given is treated with an agent which eliminates HE, or that a compound of the formula V

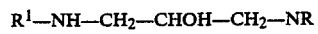    V in which R and $R^1$ have the meanings given are reacted with a reactive derivative of carbonic acid and/or that, if desired, in a compound of the formula I an O-alkyl group is cleaved to give an OH group and/or a compound of the formula I is converted by reduction to another compound of the formula I, and/or that a base of the formula I is converted to one of its salts by treatment with an acid.

The compounds of the formula I include the following compounds (in which x represents 2-, 3- or 4-position, y represents 2-, 3-, 4-, 5- or 6-position and z represents 6-, 7- or 8-position):

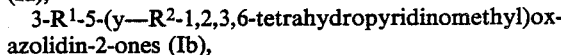

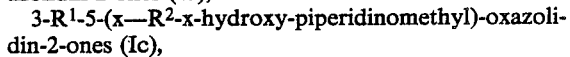

3-$R^1$-5-(x—$R^2$-CO-piperidinomethyl)-oxazolidin-2-ones (Id),

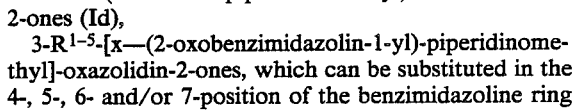

3-$R^1$-5-[x—(2-thioxobenzimidazolin-1-yl)-piperidinomethyl]-oxazolidin-2-ones, which can be substituted in the 4-, 5-, 6- and/or 7-position of the benzimidazoline ring by $R^3$ and/or $R^4$ (If), 1-$R^2$-4-oxo-z-(3-$R^1$-oxazolidin-2-on-5-yl-methyl)-1,3, z-triazaspiro[4,5]-decanes (Ig).

Preference is given to compounds of the formula Ic.
The individual compounds are

| | |
|---|---|
| Formula Ia with x = 2 | (Iaa); |
| Formula Ia with x = 3 | (Iab); |
| Formula Ia with x = 4 | (Iac); |
| Formula Ib with y = 2 | (Iba); |
| Formula Ib with y = 3 | (Ibb); |
| Formula Ib with y = 4 | (Ibc); |
| Formula Ib with y = 5 | (Ibd); |
| Formula Ib with y = 6 | (Ibe); |
| Formula Ic with x = 2 | (Ica); |
| Formula Ic with x = 3 | (Icb); |
| Formula Ic with x = 4 | (Icc); |
| Formula Id with x = 2 | (Ida); |
| Formula Id with x = 3 | (Idb); |
| Formula Id with x = 4 | (Idc); |
| Formula Ie with x = 2 | (Iea); |
| Formula Ie with x = 3 | (Ieb); |
| Formula Ie with x = 4 | (Iec); |
| Formula If with x = 2 | (Ifa); |
| Formula If with x = 3 | (Ifb); |
| Formula If with x = 4 | (Ifc); |
| Formula Ig with z = 6 | (Iga); |
| Formula Ig with z = 7 | (Igb); |
| Formula Ig with z = 8 | (Igc). |

Preference is given to compounds of the formula Icc, furthermore those of the formulae Iaa, Iab, Iac, Ibc, Ica, Icb, Idc, Iec, Ife and Igc.

In the radicals $R^1$ to $R^4$, alkyl is preferably methyl, furthermore also ethyl, n-propyl, isopropyl, n-butyl, isobutyl, sec.-butyl or tert.-butyl. Alkoxy is preferably methoxy, furthermore also ethoxy, n-propoxy, isopropoxy, n-butoxy, isobutoxy, sec.-butoxy or tert.-butoxy.

The radicals $R^1$ and $R^2$ are preferably unsubstituted or monosubstituted phenyl. If $R^1$ or $R^2$ are substituted phenyl groups, they can, however, also be disubstituted, it being possible for the substituents to be identical or different. Preferred substituents on the phenyl groups are methyl, methoxy, F, Cl or $CF_3$; furthermore, preferable substituents are ethyl, ethoxy, Br and/or OH. In detail, $R^1$ and $R^2$ are preferably phenyl, o-, m- or p-tolyl, o-, m- or p-methoxyphenyl, o-, m- or p-fluorophenyl, o-, m- or p-chlorophenyl, o-, m- or p-trifluoromethylphenyl, furthermore o-, m- or p-ethylphenyl, o-, m- or p-ethoxyphenyl, o-, m- or p-bromophenyl, o-, m- or p-hydroxyphenyl, 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4-or 3,5-dichlorophenyl, 2,3-, 2,4-, 2,5-, 2,6-, 3,4- or 3,5-dihydroxyphenyl, 2-methyl-4-chlorophenyl.

The radicals $R^1$ and $R^2$ can also be mono- or binuclear heteroaryl radicals containing 1–4 heteroatoms, which contain preferably 5 or 6 ring members in each ring. Preferably, the heteroatoms are O, S and/or N. In detail, heteroaryl radicals are preferably 2- or 3-furyl, 2- or 3-thienyl, 2-, 3- or 4-pyridyl, furthermore 1-, 2-or 3-pyrryl, 1-, 2-, 4- or 5-imidazolyl, 1-, 3-, 4- or 5-pyrazolyl, 2- 4- or 5-oxazolyl, 3-, 4- or 5-isoxazolyl, 2-, 4- or 5-thiazolyl, 3-, 4- or 5-isothiazolyl, 2-, 4-, 5- or 6-pyrimidyl, furthermore 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,2,3,4-thiadiazol-2- or -5-yl, 1,2,4-thiadiazol-3- or -5-yl, 2,1,5-thiadiazol-3- or -4-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5- 6- or 7-indolyl, 1-, 2-, 4- or 5-isoindolyl, 1-, 2-, 4- or 5-benzimidazolyl, 1-, 3-, 4-, 5-, 6- or 7benzopyrazolyl, 2-, 4-, 5-, 6- or 7-benzoxazolyl, 3-, 4-, 5-, 6- or 7-benzisoxazolyl, 2-, 4-, 5-, 6- or 7-benzothisazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolyl, 2-, 4-, 5-, 6-, 7- or 8-quinazolyl, 2-, 5- or 6-quinoxalyl.

The radical $R^1$ is very particularly preferably p-methoxyphenyl or p-fluorophenyl, the radical $R^2$ is phenyl, p-methoxyphenyl, p-fluorophenyl, p-chlorophenyl or m-trifluoromethylphenyl.

The radicals $R^3$ and $R^4$ can be identical or different. Preferably they are both H. Furthermore, one of these radicals is preferably H, the other F, Cl, OH or $CF_3$.

Accordingly, the invention relates in particular to those compounds of the formula I or Ia to Igc in which at least one of the radicals mentioned has one of the abovementioned meanings, in particular of the abovementioned preferred meanings. Some preferred groups of compounds correspond to the abovementioned formulae, in which the radicals and parameters which have not been mentioned individually have the meaning given under formula I, but in which (a) $R^1$ is phenyl, tolyl, methoxyphenyl, fluorophenyl, chlorophenyl, hydroxyphenyl, trifluoromethylphenyl or dimethoxyphenyl;

(b) $R^1$ is phenyl, o-, m- or p-tolyl, m- or p-methoxyphenyl, p-fluorophenyl, p-chlorophenyl, m- or p-hydroxyphenyl, m-trifluoromethylphenyl or 3,4-dimethoxyphenyl;

(c) $R^1$ is p-methoxyphenyl or p-fluorophenyl;

(d) $R^2$ is phenyl, tolyl, methoxyphenyl, fluorophenyl, chlorophenyl or trifluoromethylphenyl;

(e) $R^2$ is phenyl, o-, m- or p-tolyl, p-methoxyphenyl, p-fluorophenyl, p-chlorophenyl or m-trifluoromethylphenyl;

(f) $R^2$ is phenyl, p-methoxyphenyl, p-fluorophentyl, p-chlorophenyl or m-trifluoromethylphenyl;

(g) $R^1$ is phenyl, o-, m- or p-tolyl, m- or p-methoxyphenyl, p-fluorophenyl, p-chlorophenyl, m- or p-hydroxyphenyl, m-trifluoromethylphenyl or 3,4-dimethoxyphenyl and $R^2$ is phenyl, o-, m- or p-tolyl, p-methoxyphenyl, p-fluorophenyl, p-chlorophenyl or m-trifluoromethylphenyl;

(h) $R^1$ is p-methoxyphenyl or p-fluorophenyl and $R^2$ is phenyl, p-methoxyphenyl, p-fluorophenyl, p-chlorophenyl or m-trifluoromethylphenyl.

Some compounds of the formula I can have one or more asymmetric carbon atoms. Therefore, they can be present as racemates, and, if more than one asymmetric carbon atom is present, also as mixtures of a plurality of racemates and they can also be present in different optically active forms.

As for the preparation of the compounds of the formula I, it is carried out by methods known per se, such as are described in the literature (for example in the standard works such as Houben-Weyl, Methoden der Organischen Chemie (Methods of Organic Chemistry), Georg-Thieme-Verlag, Stuttgart; Organic Reactions, John Wiley & Sons, Inc., New York), under reaction conditions such as are known and suitable for the reactions mentioned. For these reactions, variations known per se which are not mentioned here in detail can also be used.

The starting materials for the process claimed can, if desired, also be formed in situ, such that they are not isolated from the reaction mixture but immediately reacted further to give the compounds of the formula I.

$X^1$ in the compounds of the formula II is preferably X; accordingly, $X^2$ and $X^3$ in the compounds of the formula III are together preferably NH. The radical X is preferably Cl or Br; but it can also be I, OH or a reactive functionally modified OH group, in particular alkylsulfonyloxy having 1–6 (for example methanesulfonyloxy) or arylsulfonyloxy having 6–10 C atoms (for example benzenesulfonyloxy, p-toluenesulfonyloxy, 1- or 2-naphthalene-sulfonyloxy).

Accordingly, the compounds of the formula I can be obtained in particular by reaction of compounds of the formulae Ox—$CH_2$—Cl, Ox—$CH_2$—Br or Ox—$CH_2$—$OSO_2CH_3$ with compounds of the formula III, in which $X^2$ and $X^3$ together represent an NH group (designated below as IIIa).

Some of the compounds of the formulae II and III are known; the unknown compounds of the formulae II and III can easily be prepared analogously to the known compounds. Primary alcohols of the formula Ox—$CH_2$—OH can be obtained, for example, by reduction of the corresponding carboxylic acids or their esters. Treatment with thionyl chloride, hydrogen bromide, phosphorus tribromide or similar halogen compounds gives the corresponding halides of the formula Ox—$CH_2$—Hal. The corresponding sulfonyloxy compounds are obtainable from the alcohols Ox—$CH_2$—OH by reaction with the corresponding sulfonyl chlorides. The iodine compounds of the formula Ox—$CH_2$—I are obtainable, for example, by the action of potassium iodide on the corresponding p-toluenesulfonic esters. The amines of the formula Ox—$CH_2$—$NH_2$ can be prepared, for example, from the halides with potassium phthalimide or by reduction of the corresponding nitriles.

The compounds of the formula IIIa are in part known (compare German Offenlegungsschrift No. 2,060,816) and can be obtained, for example, by reaction of 2-, 3- or 4-piperidone with organometallic compounds of the formula M—R² (in which M is an Li atom or MgHal), subsequent hydrolysis to give the corresponding 2-R²-2-hydroxy-, 3-R²-3-hydroxy- or 4-R²- 4-hydroxypiperidines and, if desired, subsequent dehydration to give 2-, 3- or 4-R²2,3- or -3,4-dehydro-piperidines and hydrogenation to give 2-, 3- or 4-R²-piperidines. Compounds of the formula III (X² and X³ are each X) can be prepared, for example, by reduction of appropriate diesters to give diols of the formula HO—R—OH (III, X²=X³=OH) and, if desired subsequent reaction with SOCl₂ or PBr₃.

The reaction of compounds II and III is carried out by methods such as are known from the literature for the alkylation of amines. The components can be fused with one another in the absence of a solvent, if necessary in a sealed tube or in an autoclave. However, it is also possible to react the compounds in the presence of an inert solvent. Examples of suitable solvents are hydrocarbons such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile; where appropriate even mixtures of these solvents with one another or mixtures with water. It can be advantageous to add an acid-binding agent, for example an alkali metal or alkaline earth metal hydroxide, carbonate or bicarbonate or another salt of a weak acid of the alkali metals or alkaline earth metals, preferably of potassium, sodium or calcium, or to add an organic base such as triethylamine, dimethylaniline, pyridine or quinoline or an excess of the amine component Ox—CH₂—NH₂ or of the compound of the formula IIIa. Depending on the conditions used, the reaction time is between a few minutes and 14 days, the reaction temperature between approx. 0° and 150°, usually between 20° and 130°.

Furthermore, it is possible to obtain a compound of the formula I by treating a precursor which instead of hydrogen atoms contains one or more reducible group(s) and/or one or more additional C—C and/or C—N bond(s) with a reducing agent, preferably at temperatures between −80° and +250° in the presence of at least one inert solvent.

Reducible groups (replaceable by hydrogen) are, in particular, oxygen in a carbonyl group, hydroxyl, arylsulfonyloxy (for example p-toluenesulfonyloxy), N-benzenesulfonyl, N-benzyl or O-benzyl.

In general, it is possible to convert compounds which have only one or those which have two or more of these groups or additional bonds next to each other to a compound of the formula I by reduction. Preferably, this is done by catalytic hydrogenation, by nascent hydrogen or by certain complex metal hydrides such as NaBH₄.

One group of preferred starting materials for the reduction corresponds to the formula VI

VI in which

Ox and R² have the meanings mentioned and An⊖ is an anion of a strong acid, preferably Cl⊖ or Br⊖. Compounds of the formula VI can be prepared, for example, by reaction of a compound of the formula II with a 2-, 3- or 4-R²-pyridine under the conditions given above for the reaction of II and III.

Suitable catalysts for the catalytic hydrogenation are for example noble metal, nickel and cobalt catalysts. The noble metal catalysts can be present on support materials (for example platinum or palladium on charcoal, palladium on calcium carbonate or strontium carbonate), as oxide catalysts (for example platinum oxide), or as finely divided metal catalysts. Nickel and cobalt catalysts are preferably used as Raney metals, nickel is also used on kieselguhr or pumice as support material. The hydrogenation can be carried out at room temperature and atmospheric pressure or even at elevated temperature and/or elevated pressure. Preferably, the reaction is carried out at pressures between 1 and 100 atmospheres and at temperatures between −80° and +150°, primarily between room temperature and +100°. The reaction is preferably carried out in an acidic, neutral or basic range and in the presence of a solvent such as water, methanol, ethanol, isopropanol, n-butanol, ethyl acetate, dioxane, acetic acid or THF; mixtures of these solvents with one another can also be used.

If nascent hydrogen is used as the reducing agent, it can be generated, for example, by treating metals with weak acids or with bases. Thus, for example a mixture of zinc with alkali metal hydroxide solution or of iron with acetic acid can be used. The use of sodium or another alkali metal in an alcohol such as ethanol, isopropanol, butanol, amyl or isoamyl alcohol or phenol is also suitable. Furthermore, an aluminium-nickel alloy in an alkaline-aqueous solution, with or without ethanol, can be used. Even amalgamated sodium or aluminium in an aqueous-alcoholic or aqueous solution are suitable for generating nascent hydrogen. The reaction can also be carried out in a heterogeneous phase, in which case an aqueous and a benzene or toluene phase is preferably used.

Reducing agents which can also be used are complex metal hydrides such as NaBH₄, diisobutylaluminium hydride or NaAl(OCH₂CH₂OCH₃)₂H₂ and also diborane, if desired, with the addition of catalysts such as BF₃, AlCl₃ or LiBr. Suitable solvents are, in particular, ethers such as diethyl ether, di-n-butyl ether, THF, dioxane, diglyme or 1,2-dimethoxyethane and also hydrocarbons such as benzene. Suitable solvents for a reduction with NaBH₄ are primarily alcohols such as methanol or ethanol, furthermore water and also aqueous alcohols. Using these methods, the reduction is preferably carried out at temperatures between −80° and +150°, in particular between about 0° and about 100°.

Catalytic hydrogenation of compounds of the formula VI usually gives the corresponding piperidine derivatives. If, in contrast, the compounds of the formula VI are reduced with NaBH₄, the main products are the corresponding 1,2,3,6-tetrahydropyridine derivatives.

Furthermore, compounds of the formula I in which NR is a 3- or 4-$R^2$-1,2,3,6-tetrahydropyridyl group are obtained by eliminating HE from compounds of the formula IV, which leads to the formation of a double bond. According to the definition of E, the compounds eliminated can be, for example, hydrogen halide, water (dehydration), a carboxylic acid or a different acid, ammonia or HCN. The starting materials of the formula IV are obtainable, for example, by reaction of II ($X^1=X$) with a compound of the formula $HR^5$, in which $R^5$ has the meaning given.

If one of the radicals E is Hal, this substituent can easily be eliminated under basic reaction conditions. Bases which can be used are: alkali metal hydroxides, alkali metal carbonates, alcoholates such as, for example, potassium tert.-butylate, amines, such as, for example, dimethylaniline, pyridine, collidine or quinoline; the solvents which are used are, for example, benzene, toluene, cyclohexane, THF or tert.-butanol. The amines which are used as bases can also be used in excess as a solvent. If one of the radicals E is an OH group, acids such as acetic acid, hydrochloric acid or mixtures of the two are preferably used as the water-eliminating agent. The addition of a solvent (for example water or ethanol) can be advantageous. The elimination of acyl-, alkylsulfonyl and alkoxysulfonyloxy or amino radicals can be carried out under the same conditions. Elimination of sulfo radicals, for example of mesylates or tosylates, can be carried out under mild conditions by boiling in DMF or dimethyl sulfoxide with alkali metal carbonates, for example $Li_2CO_3$, or with potassium acetate. Ammonia can be eliminated simply by heating the salts of the corresponding amino compounds (in particular of the 4-amino derivatives).

In a similar manner, HCN can be eliminated from compounds of the formula IV (a group E=CN) by heating. Elimination of HE from IV occurs in general at temperatures between 0° and about 250°, preferably between 50° and 200°.

Compounds of the formula I are also obtainable by reaction of amino alcohols of the formula V with reactive derivatives of carbonic acid. Suitable examples of those are preferably dialkyl carbonates such as dimethyl or diethyl carbonate, esters of chloroformic acid such as methyl or ethyl chloroformate, N,N'-carbonyldiimidazole or phosgene. The reaction is preferably achieved in the presence of an inert solvent, preferably of a halogenated hydrocarbon such as chloroform, of a hydrocarbon such as toluene or of an amide such as DMF at temperatures between about 20° and about 200°, preferably between 100° and 150°. The carbonic acid derivative is preferably used in excess. Amino alcohols V are obtainable, for example, by reaction of amines of the formula $R^1$—$NH_2$ with epichlorohydrin to give ($R^1$-aminomethyl)-ethylene oxides and subsequent reaction with compounds of the formula IIIa.

Furthermore, a compound of the formula I can, if desired, be converted by methods known per se to another compound of the formula I.

Thus ethers (O-alkyl derivatives) can be cleaved, giving the corresponding hydroxy derivatives. For example, the ethers can be cleaved by treatment with the dimethyl sulfide-boron tribromide complex, for example in toluene, 1,2-dichloroethane, THF or dimethyl sulfoxide, by fusion with pyridinium or anilinium hydrohalides, preferably pyridinium hydrochloride, at about 150°–250°, with HBr/acetic acid or with Al trihalides in chlorinated hydrocarbons such as 1,2-dichloroethane.

After a base of the formula I has been obtained, it can be converted with an acid to the corresponding acid addition salt. Acids suitable for this reaction are preferably those which give physiologically safe salts. Thus, inorganic acids can be used, for example sulfuric acid, hydrohalic acids such as hydrochloric acid or hydrobromic acid, phosphoric acids such as orthophosphoric acids, nitric acid, sulfamic acid, furthermore organic acids, in detail aliphatic, alicyclic, araliphatic, aromatic or heterocyclic mono- or polybasic carboxylic, sulfonic or sulfuric acids such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid. Acid addition salts which are not physiologically safe (for example picrates) can be suitable for the isolation and purification of bases of the formula I.

The free bases of the formula I can, if desired, be liberated from their salts by treatment with strong bases such as sodium hydroxide or potassium hydroxide and sodium carbonate or potassium carbonate.

The invention further relates to the use of compounds of the formula I and their physiologically safe salts for preparing pharmaceutical preparations, in particular by non-chemical methods. For this purpose, they can be brought into a suitable dosage form together with at least one carrier or auxiliary and, if desired, in combination with one or more further active substance(s).

The invention further relates to agents, in particular pharmaceutical preparations, containing at least one compound of the formula I and/or one of its physiologically safe salts. These preparations can be used as medicaments in human and veterinary medicine. Examples of carrier materials are organic or inorganic substances which are suitable for the enteral (for example oral), parenteral or topical application and do not react with the novel compounds, for example water, vegetable oils, benzyl alcohols, polyethylene glycols, gelatin, carbohydrates such as lactose or starch, magnesium stearate, talc, and paraffin jelly; Suitable for enteral application are, in particular, tablets, coated pills, capsules, syrups, juices, drops or suppositories, for parenteral application solutions, preferably oily or aqueous solutions, furthermore suspensions, emulsions or implants, and for topical application ointments, creams or powders. The novel compounds can also be freeze-dried, and the freeze-dried compounds obtained can be used, for example, for preparing injection preparations.

The preparations mentioned can be sterilized and/or contain auxiliaries such as lubricants, preservatives, stabilizers and/or wetting agents, emulsifiers, salts for influencing the osmotic pressure, buffer substances, colorants, flavorings and/or aromas. If desired, they can also contain one or more further active substances, for example one or more vitamins.

The compounds of the formula I and their physiologically safe salts can be used for the therapeutic treatment of the human or animal body and for fighting diseases, in particular schizophrenia and psychoreactive disturbances and psychopathies, depressions, severe chronic pains and diseases which are accompanied by high blood pressure. The compounds can further be used for the treatment of extrapyramidal disturbances.

The substances according to the invention are usually given by analogy with known, commercially available products (thioridazine, haloperidol), preferably in dosage amounts between about 0.2 and 500 mg, in particular between 0.2 and 50 mg per dosage unit. The daily dosage is preferably between about 0.003 and 10 mg/kg of body weight.

The specific dose amount for each individual patient depends, however, on a wide variety of factors, for example on the activity of the specific compound used, on age, body weight, general state of health, sex, on the food, on the date and route of application, on the rate of excretion, medicament combination and seriousness of disease in question for which the therapy is intended. Preference is given to oral application.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

In the following examples, "conventional workup" means: if necessary, water is added, the product is extracted with dichloromethane, and separated off, the organic phase is dried over sodium sulfate, filtered, evaporated, and the residue is purified by chromatography over silica gel and/or by crystallization.

EXAMPLE 1

4.82 g of 5-methanesulfonyloxymethyl-3-p-methoxyphenyl-oxazolidin-2-one [m.p. 126°–128°; obtainable by reaction of p-methoxyaniline with hydroxymethyloxirane to give 3-p-methoxyanilino-1,2-propanediol, reaction with diethyl carbonate to give 3-p-methoxyphenyl-5-hydroxymethyl-oxazolidin-2-one (m.p. 133°–134°) and reaction with $CH_3SO_2Cl$] is heated together with 5.08 g of 4-p-chlorophenyl-4-hydroxypiperidine in 25 ml of DMF at 95°–100° for 1 hour; the mixture is cooled and worked up in a conventional manner to give 3-p-methoxyphenyl-5-(4-p-chlorophenyl-4-hydroxy-piperidinomethyl)-oxazolidin-2-one, m.p. 143°–144°.

The following examples are obtained analogously from the corresponding 5-hydroxymethyl-3-$R^1$-oxazolidin-2-ones:

5-hydroxymethyl-3-p-fluorophenyl-oxazolidin-2-one (m.p. 107°–108°)
5-hydroxymethyl-3-p-chlorophenyl-oxazolidin-2-one (m.p. 113°–115°)
5-hydroxymethyl-3-m-trifluoromethylphenyl-oxazolidin-2-one (m.p. 73°–76°)
5-hydroxymethyl-3-(3,4-dimethoxyphenyl)-oxazolidin-2-one (m.p. 153°–154°) via the corresponding 5-methanesulfonyloxymethyl-, 5-chloromethyl- or 5-bromomethyl-3-$R^1$-oxazolidin-2-ones of the formula II, for example:

5-chloromethyl-3-p-methoxyphenyl-oxazolidin-2-one (m.p. 98°–100°)
5-methanesulfonyloxymethyl-3-p-fluorophenyl-oxazolidin-2-one (m.p. 136°)
5-methanesulfonyloxymethyl-3-p-chlorophenyl-oxazolidin-2-one (m.p. 123°–125°)
5-methanesulfonyloxymethyl-3-m-trifluoromethylphenyl-oxazolidin-2-one (m.p. 70°–71°)
5-methanesulfonyloxymethyl-3-(3,4-dimethoxyphenyl)-oxazolidin-2-one (m.p. 147°–149°) with the corresponding piperidine derivatives of the formula III (in which $X^2$ and $X^3$ together are NH):

3-phenyl-5-(4-phenyl-piperidino-methyl)-oxazolidin-2-one. m.p. 122°–123°
3-phenyl-5-(2-benzyl-piperidino-methyl)-oxazolidin-2-one
3-m-tolyl-5-(2-benzyl-piperidino-methyl)-oxazolidin-2-one
3-o-methoxyphenyl-5-(2-benzyl-piperidino-methyl)-oxazolidin-2-one
3-m-methoxyphenyl-5-(2-benzyl-piperidino-methyl)-oxazolidin-2-one
3-p-methoxyphenyl-5-(2-benzyl-piperidino-methyl)-oxazolidin-2-one, 2 diastereomers, hydrochlorides, decomposition above 200° and decomposition above 205°
3-p-fluorophenyl-5-(2-benzyl-piperidino-methyl)-oxazolidin-2-one, 2 diastereomers, hydrochlorides, m.p. 207°–208° and m.p. 209°–210°
3-p-chlorophenyl-5-(2-benzyl-piperidino-methyl)-oxazolidin-2-one
3-m-trifluoromethylphenyl-5-(2-benzyl-piperidino-methyl)-oxazolidin-2-one
3-(3,4-dimethoxyphenyl)-5-(2-benzyl-piperidino-methyl)-oxazolidin-2-one
3-phenyl-5-(3-benzyl-piperidino-methyl)-oxazolidin-2-one
3-m-tolyl-5-(3-benzyl-piperidino-methyl)-oxazolidin-2-one
3-o-methoxyphenyl-5-(3-benzyl-piperidino-methyl)-oxazolidin-2-one
3-m-methoxyphenyl-5-(3-benzyl-piperidino-methyl)-oxazolidin-2-one
3-p-methoxyphenyl-5-(3-benzyl-piperidino-methyl)-oxazolidin-2-one, hydrochloride hydrate, m.p. above 139° (decomposition)
3-p-fluorophenyl-5-(3-benzyl-piperidino-methyl)-oxazolidin-2-one, hydrochloride, m.p. 215°–218° (decomposition)
3-p-chlorophenyl-5-(3-benzyl-piperidino-methyl)-oxazolidin-2-one
3-m-trifluoromethylpnenyl-5-(3-benzyl-piperidino-methyl)-oxazolidin-2-one
3-(3,4-dimethoxyphenyl)-5-(3-benzyl-piperidino-methyl)-oxazolidin-2-one
3-phenyl-5-(4-benzyl-piperidino-methyl)-oxazolidin-2-one
3-m-tolyl-5-(4-benzyl-piperidino-methyl)-oxazolidin-2-one
3-o-methoxyphenyl-5-(4-benzyl-piperidino-methyl)-oxazolidin-2-one
3-m-methoxyphenyl-5-(4-benzyl-piperidino-methyl)-oxazolidin-2-one
3-p-methoxyphenyl-5-(4-benzyl-piperidino-methyl)-oxazolidin-2-one hydrochloride, m.p. above 209° (decomposition)

3-p-fluorophenyl-5-(4-benzyl-piperidino-methyl)-oxazolidin-2-one hydrochloride, m.p. 224°–225°
3-p-chlorophenyl-5-(4-benzyl-piperidino-methyl)-oxazolidin-2-one
3-m-trifluoromethylphenyl-5-(4-benzyl-piperidino-methyl)-oxazolidin-2-one
3-(3,4-dimethoxyphenyl)-5-(4-benzyl-piperidino-methyl)-oxazolidin-2-one
3-phenyl-5-(4-hydroxy-4-phenyl-piperidino-methyl)-oxazolidin-2-one
3-m-tolyl-5-(4-hydroxy-4-phenyl-piperidino-methyl)-oxazolidin-2-one, m.p. 121°–122°
3-o-methoxyphenyl-5-(4-hydroxy-4-phenyl-piperidino-methyl)-oxazolidin-2-one
3-m-methoxyphenyl-5-(4-hydroxy-4-phenyl-piperidino-methyl)-oxazolidin-2-one
3-p-methoxyphenyl-5-(4-hydroxy-4-phenyl-piperidino-methyl)-oxazolidin-2-one, m.p. 141°–143°
3-p-fluorophenyl-5-(4-hydroxy-4-phenyl-piperidino-methyl)-oxazolidin-2-one, m.p. 126°–128°
3-p-chlorophenyl-5-(4-hydroxy-4-phenyl-piperidino-methyl)-oxazolidin-2-one, m.p. 144°–146°
3-m-trifluoromethylphenyl-5-(4-hydroxy-4-phenyl-piperidino-methyl)-oxazolidin-2-one, hydrochloride, m.p. 247°–249° (decomposition)
3-(3,4-dimethoxyphenyl)-5-(4-hydroxy-4-phenyl-piperidino-methyl)-oxazolidin-2-one
3-phenyl-5-(4-hydroxy-4-p-methoxyphenyl-piperidino-methyl)-oxazolidin-2-one
3-m-tolyl-5-(4-hydroxy-4-p-methoxyphenyl-piperidino-methyl)-oxazolidin-2-one, m.p. 121–122°
3-o-methoxyphenyl-5-(4-hydroxy-4-p-methoxyphenyl-piperidino-methyl)-oxazolidin-2-one
3-m-methoxyphenyl-5-(4-hydroxy-4-p-methoxyphenyl-piperidino-methyl)-oxazolidin-2-one
3-p-methoxyphenyl-5-(4-hydroxy-4-p-methoxyphenyl-piperidino-methyl)-oxazolidin-2-one, m.p. 158°–160°
3-p-fluorophenyl-5-(4-hydroxy-4-p-methoxyphenyl-piperidino-methyl)-oxazolidin-2-one
3-p-chlorophenyl-5-(4-hydroxy-4-p-methoxyphenyl-piperidino-methyl)-oxazolidin-2-one, m.p. 139°–140°
3-m-trifluoromethylphenyl-5-(4-hydroxy-4-p-methoxyphenyl-piperidino-methyl)-oxazolidin-2-one
3-(3,4-dimethoxyphenyl)-5-(4-hydroxy-4-p-methoxyphenyl-piperidino-methyl)-oxazolidin-2-one
3-phenyl-5-(4-hydroxy-4-p-fluorophenyl-piperidino-methyl)-oxazolidin-2-one
3-m-tolyl-5-(4-hydroxy-4-p-fluorophenyl-piperidino-methyl)-oxazolidin-2-one, m.p. 128°–129°
3-o-methoxyphenyl-5-(4-hydroxy-4-p-fluorophenyl-piperidino-methyl)-oxazolidin-2-one
3-m-methoxyphenyl-5-(4-hydroxy-4-p-fluorophenyl-piperidino-methyl)-oxazolidin-2-one, m.p. 116°–118°
3-p-methoxyphenyl-5-(4-hydroxy-4-p-fluorophenyl-piperidino-methyl)-oxazolidin-2-one
3-p-fluorophenyl-5-(4-hydroxy-4-p-fluorophenyl-piperidino-methyl)-oxazolidin-2-one
3-p-chlorophenyl-5-(4-hydroxy-4-p-fluorophenyl-piperidino-methyl)-oxazolidin-2-one, m.p. 145°–147°
3-m-trifluoromethylphenyl-5-(4-hydroxy-4-p-fluorophenyl-piperidino-methyl)-oxazolidin-2-one
3-(3,4-dimethoxyphenyl)-5-(4-hydroxy-4-p-fluorophenyl-piperidino-methyl)-oxazolidin-2-one
3-phenyl-5-(4-hydroxy-4-p-chlorophenyl-piperidino-methyl)-oxazolidin-2-one
3-m-tolyl-5-(4-hydroxy-4-p-chlorophenyl-piperidino-methyl)-oxazolidin-2-one, m.p. 139°–140°
3-o-methoxyphenyl-5-(4-hydroxy-4-p-chlorophenyl-piperidino-methyl)-oxazolidin-2-one
3-m-methoxyphenyl-5-(4-hydroxy-4-p-chlorophenyl-piperidino-methyl)-oxazolidin-2-one, m.p. 114°–115°
3-p-methoxyphenyl-5-(4-hydroxy-4-p-chlorophenyl-piperidino-methyl)-oxazolidin-2-one, m.p. 143°–144°
3-p-fluorophenyl-5-(4-hydroxy-4-p-chlorophenyl-piperidino-methyl)-oxazolidin-2-one, m.p. 134°–136°
3-p-chlorophenyl-5-(4-hydroxy-4-p-chlorophenyl-piperidino-methyl)-oxazolidin-2-one, m.p. 163°–164°
3-m-trifluoromethylphenyl-5-(4-hydroxy-4-p-chlorophenyl-piperidino-methyl)-oxazolidin-2-one, hydrochloride, m.p. 235°–237°
3-(3,4-dimethoxyphenyl)-5-(4-hydroxy-4-p-chlorophenyl-piperidino-methyl)-oxazolidin-2-one, m.p. 123°–125°
3-phenyl-5-(4-hydroxy-4-m-trifluoromethylphenyl-piperidino-methyl)-oxazolidin-2-one
3-m-tolyl-5-(4-hydroxy-4-m-trifluoromethylphenyl-piperidino-methyl)-oxazolidin-2-one, m.p. 136°–137°
3-o-methoxyphenyl-5-(4-hydroxy-4-m-trifluoromethylphenyl-piperidino-methyl)-oxazolidin-2-one
3-m-methoxyphenyl-5-(4-hydroxy-4-m-trifluoromethylphenyl-piperidino-methyl)-oxazolidin-2-one
3-p-methoxyphenyl-5-(4-hydroxy-4-m-trifluoromethylphenyl-piperidino-methyl)-oxazolidin-2-one, m.p. 137°–138°
3-p-fluorophenyl-5-(4-hydroxy-4-m-trifluoromethylphenyl-piperidino-methyl)-oxazolidin-2-one, m.p. 147°–148°
3-p-chlorophenyl-5-(4-hydroxy-4-m-trifluoromethylphenyl-piperidino-methyl)-oxazolidin-2-one
3-m-trifluoromethylphenyl-5-(4-hydroxy-4-m-trifluoromethyl-phenyl-piperidino-methyl)-oxazolidin-2-one, m.p. 114°–116°
3-(3,4-dimethoxyphenyl)-5-(4-hydroxy-4-m-trifluoromethyl-phenyl-piperidino-methyl)-oxazolidin-2-one
3-phenyl-5-(4-benzyl-4-hydroxy-piperidino-methyl)-oxazolidin-2-one
3-phenyl-5-(4-benzoyl-piperidino-methyl)-oxazolidin-2-one
3-m-tolyl-5-(4-benzoyl-piperidino-methyl)-oxazolidin-2-one, m.p. 104°–105°
3-o-methoxyphenyl-5-(4-benzoyl-piperidino-methyl)-oxazolidin-2-one
3-m-methoxyphenyl-5-(4-benzoyl-piperidino-methyl)-oxazolidin-2-one, hydrochloride, m.p. 261°–263°-(decomposition)
3-p-methoxyphenyl-5-(4-benzoyl-piperidino-methyl)-oxazolidin-2-one, m.p. 130°–132°
3-p-fluorophenyl-5-(4-benzoyl-piperidino-methyl)-oxazolidin-2-one
3-p-chlorophenyl-5-(4-benzoyl-piperidino-methyl)-oxazolidin-2-one
3-m-trifluoromethylphenyl-5-(4-benzoyl-piperidino-methyl)-oxazolidin-2-one
3-(3,4-dimethoxyphenyl)-5-(4-benzoyl-piperidino-methyl)-oxazolidin-2-one, m.p. 131°–133°
3-phenyl-5-[4-(2-oxobenzimidazolin-1-yl)-piperidino-methyl]-oxazolidin-2-one
3-m-tolyl-5-[4-(2-oxobenzimidazolin-1-yl)-piperidino-methyl]-oxazolidin-2-one, m.p. 210°–212°
3-o-methoxyphenyl-5-[4-(2-oxobenzimidazolin-1-yl)-piperidinomethyl]-oxazolidin-2-one
3-m-methoxyphenyl-5-[4-(2-oxobenzimidazolin-1:yl)-piperidinomethyl]-oxazolidin-2-one, m.p. 168°–170°

3-p-methoxyphenyl-5-[4-(2-oxobenzimidazolin-1-yl)-
  piperidinomethyl]-oxazolidin-2-one, m.p. 211°-212°
3-p-fluorophenyl-5-[4-(2-oxobenzimidazolin-1-yl)-
  piperidinomethyl]-oxazolidin-2-one, m.p. 216°-217°
3-p-chlorophenyl-5-[4-(2-oxobenzimidazolin-1-yl)-
  piperidinomethyl]-oxazolidin-2-one
3-m-trifluoromethylphenyl-5-[4-(2-oxobenzimidazolin-
  1-yl)-piperidinomethyl]-oxazolidin-2-one, m.p.
  195°-196°
3-(3,4-dimethoxyphenyl)-5-[4-(2-oxobenzimidazolin-1-
  yl)-piperidinomethyl]-oxazolidin-2-one, m.p.
  199°-201°
3-phenyl-5-[4-(2-thioxobenzimidazolin-1-yl)-piperidino-
  methyl]-oxazolidin-2-one
3-m-tolyl-5-[4-(2-thioxobenzimidazolin-1-yl)-
  piperidinomethyl]-oxazolidin-2-one
3-o-methoxyphenyl-5-[4-(2-thioxobenzimidazolin-1-yl)-
  piperidinomethyl]-oxazolidin-2-one
3-m-methoxyphenyl-5-[4-(2-thioxobenzimidazolin-1-
  yl)-piperidinomethyl]-oxazolidin-2-one
3-p-methoxyphenyl-5-[4-(2-thioxobenzimidazolin-1-yl)-
  piperidinomethyl]-oxazolidin-2-one
3-p-fluorophenyl-5-[4-(2-thioxobenzimidazolin-1-yl)-
  piperidinomethyl]-oxazolidin-2-one
3-p-chlorophenyl-5-4-(2-thioxobenzimidazolin-1-yl)-
  piperidinomethyl]-oxazolidin-2-one
3-m-trifluoromethylphenyl-5-[4-(2-thioxobenzimidazo-
  lin-1-yl)-piperidinomethyl]-oxazolidin-2-one
3-(3,4-dimethoxyphenyl)-5-[4-(2-thioxobenzimidazolin-
  1-yl)-piperidinomethyl]-oxazolidin-2-one
1-phenyl-4-oxo-8-(3-phenyl-oxazolidin-2-on-5-yl-
  methyl)-1,3,8-triazaspiro[4,5]decane
1-phenyl-4-oxo-8-(3-m-tolyl-oxazolidin-2-on-5-yl-
  methyl)-1,3,8-triazaspiro[4,5]decane, m.p. 166°-168°
1-phenyl-4-oxo-8-(3-o-methoxyphenyl-oxazolidin-2-on-
  5-yl-methyl)-1,3,8-triazaspiro[4,5]decane
1-phenyl-4-oxo-8-(3-m-methoxyphenyl-oxazolidin-
  2-on-5-yl-methyl)-1,3,8-triazaspiro[4,5]decane, m.p.
  157°-158°
1-phenyl-4-oxo-8-(3-p-methoxyphenyl-oxazolidin-2-on-
  5-yl-methyl)-1,3,8-triazaspiro[5]decane, m.p.
  192°-193°
1-phenyl-4-oxo-8-(3-p-fluorophenyl-oxazolidin-2-on-
  5-yl-methyl)-1,3,8-triazaspiro[4,5]decane, m.p.
  220°-222°
1-phenyl-4-oxo-8-(3-p-chlorophenyl-oxazolidin-2-on-
  5-yl-methyl)-1,3,8-triazaspiro[4,5]decane
1-phenyl-4-oxo-8-(3-m-trifluoromethylphenyl-oxazoli-
  din-2-on-5-yl-methyl)-1,3,8-triazaspiro[4,5]decane,
  m.p. 188°-190°
1-phenyl-4-oxo-8-[3-(3,4-dimethoxyphenyl)-oxazolidin-
  2-on-5-yl-methyl]-1,3,8-triazaspiro[4,5]decane, m.p.
  192°-194°

EXAMPLE 2

A mixture of 1.92 g of 5-aminomethyl-3-phenylox-
azolidin-2-one [obtainable by reaction of phenyl isocya-
nate with 1,3-dichloro-2-propanol in the presence of
$AlCl_3$ to give 1,3-dichloro-2-propyl N-phenylcarba-
mate, cyclization with aqueous KOH at 100° to give
5-chloromethyl-3-phenyl-oxazolidin-2-one, reaction
with potassium phthalimide followed by hydrolysis]
and 2.15 g of 1,5-dichloro-3-phenyl-2-pentene in 40 ml
of acetone and 40 ml of water is boiled for 24 hours and
worked up in a conventional manner. This gives 3-phe-
nyl-5-(4-phenyl-1,2,3,6-tetrahydropyridyl-1-methyl)-
oxazolidin-2-one.

EXAMPLE 3

1 g of $NaBH_4$ in 20 ml of water is added to a solution
of 4.41 g of 1-(3-p-methoxyphenyl-oxazolidin-2-on-5-yl-
methyl)-4-phenyl-pyridinium bromide (obtainable from
3-p-methoxyphenyl-5-bromomethyl-oxazolidin-2-one
and 4-phenylpyridine) in 50 ml of 1 N NaOH, and the
mixture is then stirred at 60° for 3 hours. A conventional
workup gives 3-p-methoxyphenyl-5-(4-phenyl-1,2,3,6-
tetra- hydropyridyl-1-methyl)-oxazolidin-2-one.

EXAMPLE 4

1 g of 3-p-methoxyphenyl-5-(4-hydroxy-4-phenyl-
piperidino-methyl)-oxazolidin-2-one is heated with 10
ml of 1 N hydrochloric acid to 100° for 2 hours; the
mixture is worked up in a conventional manner to give
3-p-methoxyphenyl-5-(4-phenyl-1,2,3,6-tetrahydropyri-
dyl-1-methyl)-oxazolidin-2-one.

EXAMPLE 5

A mixture of 3.56 g of 4-hydroxy-1-(2-hydroxy-3-p-
methoxyanilino-propyl)-4-phenyl-piperidine (obtain-
able by reaction of p-methoxyaniline with ethyl 2,3-
epoxypropionate to give ethyl 2-hydroxy-3-p-methox-
yanilinopropionate, reduction with $LiAlH_4$ to give 3-p-
methoxy-anilino-1,2-propanediol, dehydration to the
epoxide and reaction with 4-hydroxy-4-phenyl-piperi-
dine), 1.5 g of diethyl carbonate and 50 ml of DMF is
heated at 120° for 4 hours. Evaporation and conven-
tional workup gives 3-p-methoxyphenyl-5-(4-hydroxy-
4-phenyl-piperidino-methyl)-oxazolidin-2-one, m.p.
141°-143°

EXAMPLE 6

A mixture of 10 g of 3-p-methoxyphenyl-5-(4-phenyl-
1,2,3,6-tetrahydropyridyl-1-methyl)-oxazolidin-2-one
and 10 g of pyridinium hydrochloride is stirred at 160°
for 3 hours. Conventional workup gives 3-p-hydrox-
yphenyl-5-(4-phenyl-1,2,3,6-tetrahydropyridyl-1-
methyl)-oxazolidin-2-one.

EXAMPLE 7

A suspension of 3.8 g of 3-p-methoxyphenyl-5-(4-ben-
zyl-piperidino-methyl)-oxazolidin-2-one in 50 ml of
1,2-dichloroethane is added dropwise to a boiling solu-
tion of 15.6 g of dimethyl sulfide/boron tribromide
complex in 50 ml of 1,2-dichloroethane; the mixture is
boiled for another 30 minutes and worked up in a con-
ventional manner to give 3-p-hydroxyphenyl-5-(4-ben-
zyl-piperidino-methyl)-oxazolidin-2-one.

EXAMPLE 8

Analogously to Example 1 there are obtained
3-p-methoxyphenyl-5-(4-phenyl-piperidino-methyl)-
  oxazolidin-2-one, m.p. 154°-156°
3-p-fluorophenyl-5-(4-phenyl-piperidino-methyl)-
  oxazolidin-2-one, m.p. 143°-145°
3-p-hydroxyphenyl-5-(4-hydroxy-4-p-methoxyphenyl-
  piperidino-methyl)-oxazolidin-2-one, m.p. 136°-138°
3-p-hydroxyphenyl-5-(4-p-methoxyphenyl-piperidino-
  methyl)-oxazolidin-2-one, m.p. 137°-138°
3-p-methoxyphenyl-5-(4-hydroxy-4-p-trimethylacetox-
  yphenyl-piperidino-methyl)-oxazolidin-2-one, m.p.
  170°-172°
3-p-methylthiophenyl-5-(4-hydroxy-4-p-methoxyphe-
  nyl-piperidino-methyl)-oxazolidin-2-one. m.p.
  137°-139°

3-p-methylsulfinylphenyl-5-(4-hydroxy-4-p-methoxyphenyl-piperidino-methyl)-oxazolidin-2-one, m.p. 161°–162°

3-p-methylsulfonylphenyl-5-(4-hydroxy-4-p-methoxyphenyl-piperidino-methyl)-oxazolidin-2-one, m.p. 212°–213°

3-p-methoxyphenyl-5-(4-hydroxy-4-p-chlorophenyl-piperidino-methyl)-oxazolidin-2-one, m.p. 142° (dec.)

3-p-acetamidophenyl-5-(4-hydroxy-4-p-methoxyphenyl-piperidino-methyl)-oxazolidin-2-one, m.p. 235°–237°

3-p-acetamidophenyl-5-(4-hydroxy-4-p-chlorophenyl-piperidino-methyl)-oxazolidin-2-one, m.p. 230°–232°.

EXAMPLE 9

Analogously to Example 1 there are obtained 3-p-methoxyphenyl-5-(4-hydroxy-4-phenyl-piperidino-methyl)-oxazolidin-2-one, S-(−)-form, m.p. 154°–155°; $[\alpha]_D^{20}$ −14.2° (chloroform)

R-(+)-form, m.p. 156°–157°; $[\alpha]_D^{20}$ +14.6° (chloroform)

3-p-methoxyphenyl-5-(4-hydroxy-4-p-methoxyphenyl-piperidino-methyl)-oxazolidin-2-one, S-(−)-form, m.p. 136°–138°; $[\alpha]_D^{20}$ −12.9° (chloroform)

R-(+)-form, m.p. 137°–138°; $[\alpha]_D^{20}$ +13.7° (chloroform)

3-p-methoxyphenyl-5-(4-hydroxy-4-p-chlorophenyl-piperidinomethyl)-oxazolidin-2-one, S-(−)-form, m.p. 140°–141°; $[\alpha]_D^{20}$ −13.9° (chloroform)

R-(+)-form, m.p. 140°–141°; $[\alpha]_D^{20}$ +12.8° (chloroform).

The starting materials can be obtained as follows:

R-(−)- and S-(+)-1,2-O-isopropylideneglycerol are each reacted with p-toluolsulfonyl chloride/pyridine to yield the oily p-toluenesulfonates and these are reacted with p-methoxyaniline to give the oily 2,2-dimethyl-4-p-methoxyanilino-1,3-dioxolanes. By acid hydrolysis one obtains therefrom the two epimeric 1-p-methoxyanilinopropane-2,3-diols (R-form, m.p. 74°–77°; $[\alpha]_D^{20}$ +11.8° in chloroform; S-form, m.p. 79°–80°; $[\alpha]_D^{20}$ −12.5° in chlorochloroform; which are transformed with diethyl carbonate/Na into the epimeric 3-p-methoxyphenyl-5-hydroxymethyl-oxazolidin-2-ones (R-form, m.p. 164°–165°; $[\alpha]_D^{20}$ −49.8 in DMSO; S-form, m.p.163°–164°; $[\alpha]_D^{20}$ +51.4° in DMSO) and then with methane sulfonyl chloride/pyridine into the corresponding methanesulfonates (R-form, m.p. 149°–150°; $[\alpha]_D^{20}$ −54.6° in DMSO; S-form, m.p. 150°–151°; $[\alpha]_D^{20}$ +56.5° in DMSO).

The following examples deal with pharmaceutical preparations which contain amines of the formula I or their acid addition salts:

EXAMPLE A

Tablets

A mixture of 1 kg of 3-p-methoxyphenyl-5-(4-hydroxy-4-p-chlorophenyl-piperidino-methyl)-oxazolidin-2-one, 4 kg of lactose, 1.2 kg of potato starch, 0.2 kg of talc and 0.1 kg of magnesium stearate is compressed into tablets in a conventional manner and in such a way that each tablet contains 10 mg of active substance.

EXAMPLE B

Coated pills

Analogously to Example A, tablets are pressed and then coated in a conventional manner with a coating consisting of saccharose, potato starch, talc, tragacanth and colorant.

EXAMPLE C

Capsules 2 kg of 3-p-methoxyphenyl-5-(4-hydroxy-4-phenyl-piperidino-methyl)-oxazolidin-2-one are filled in a conventional manner into hardened gelatin capsules so that each capsule contains 20 mg of active substance.

EXAMPLE D

Capsules

A solution of 1 kg of 3-p-fluorophenyl-5-(4-benzyl-piperidino-methyl)-oxazolidin-2-one hydrochloride in 60 l of twice-distilled water is filtered under sterile conditions, filled into ampoules, freeze-dried under sterile conditions and sealed under sterile conditions. Each ampoule contains 10 mg of active substance.

Analogously tablets, coated pills, capsules and ampoules are obtainable which contain one or more of the remaining active substances of the formula I and/or their physiologically safe acid addition salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. An oxazolidinone of the formula

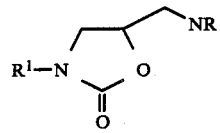

wherein R is

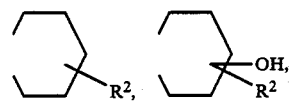

or

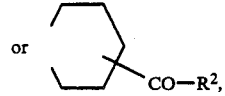

$R^1$ and $R^2$ are each independently phenyl or phenyl mono- or disubstituted by $C_{1-4}$-alkyl, $C_{1-4}$-alkoxy, $C_{1-4}$-alkylthio, $C_{1-4}$-alkylsulfinyl, $C_{1-4}$-alkylsulfonyl, $C_{1-6}$-alkanoyloxy, $C_{1-6}$-alkanoylamino, F, Cl, Br, OH, $CF_3$ or a mixture thereof, or a physiologically acceptable salt of said oxazolidinone.

2. An oxazolidinone according to claim 1, wherein $R^1$ and $R^2$ are each independently phenyl or phenyl monosubstituted by methyl, methoxy, F, Cl, $CF_3$, ethyl, ethoxy, Br or OH.

3. An oxazolidinone according to claim 2, wherein $R^1$ and $R^2$ are phenyl, o-, m- or p-tolyl, o-, m- or p-methoxyphenyl, o-, m- or p-fluorophenyl, o-, m- or p-chlorophenyl, o-, m- or p-trifluoromethylphenyl, o-, m- or p-ethylphenyl, o-, m- or p-ethoxyphenyl, o-, m- or p-bromophenyl, o-, m- or p-hydroxyphenyl, 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6, 3,4- or 3,5-dichlorophenyl, 2,3-, 2,4-, 2,5-, 2,6-, 3,4- or 3,5-dihydroxyphenyl or 2-methyl-4-chlorophenyl.

4. An oxazolidinone according to claim 3, wherein $R^1$ is p-methoxyphenyl or p-fluorophenyl, and $R^2$ is phenyl, p-methoxyphenyl, p-fluorophenyl, p-chlorophenyl or m-trifluoromethylphenyl.

5. An oxazolidinone according to claim 1 of the formula
  (a) 3-$R^1$-5-(x—$R^2$-piperidinomethyl)-oxazolidin-2-one,
  (b) 3-$R^1$-5-(x—$R^2$-CO-piperidinomethyl)-oxazolidin-2-one, 6. A compound according to claim 1, said compound being
  (a) 3-p-methoxyphenyl-5-(4-hydroxy-4-m-trifluoromethyl-phenyl-piperidino-methyl)-oxazolidin-2-one;
  (b) 3-p-fluorophenyl-5-(4-hydroxy-4-m-trifluoromethyl-phenyl-piperidino-methyl)-oxazolidin-2-one;
  (c) 3-p-fluorophenyl-5-(4-hydroxy-4-p-chlorophenyl-piperidinomethyl)-oxazolidin-2-one;
  (d) 3-p-methoxyphenyl-5-(4-hydroxy-4-p-chlorophenyl-piperidinomethyl)-oxazolidin-2-one;
  (e) 3-p-methoxyphenyl-5-(4-hydroxy-4-phenyl-piperidino-methyl)-oxazolidin-2-one;
  (f) 3-p-methoxyphenyl-5-(4-hydroxy-4-p-methoxyphenyl-piperidinomethyl)-oxazolidin-2-ones;
  or (g) 3-p-methoxyphenyl-5-(4-hydroxy-4-p-fluorophenyl-piperidinomethyl)-oxazolidin-2-one.

7. A pharmaceutical composition comprising a compound of claim 1 and a pharmaceutically acceptable carrier.

8. A pharmaceutical composition comprising a compound of claim 6 and a pharmaceutically acceptable carrier.

* * * * *